United States Patent [19]

Ohno et al.

[11] 4,336,808
[45] Jun. 29, 1982

[54] ULTRASONIC WAVE PROBE

[75] Inventors: Mitio Ohno, Kawasaki; Yoichi Shimada, Yokohama; Hiroshi Furuhata, Kasukabe; Ryoichi Kanno, Funabashi; Kuniyasu Kodaira; Hirozi Matumoto, both of Kawasaki, all of Japan

[73] Assignees: Shozo Yoshimura; Hayashi Denki Co. Ltd., both of Kawasaki, all of Japan

[21] Appl. No.: 140,852

[22] Filed: Apr. 16, 1980

[30] Foreign Application Priority Data

Apr. 24, 1979 [JP] Japan ............................ 54-55342[U]

[51] Int. Cl.³ ................................................ A61B 10/00
[52] U.S. Cl. .................................... 128/663; 73/861; 73/25
[58] Field of Search ............................. 128/660–663; 73/861, 25

[56] References Cited

U.S. PATENT DOCUMENTS

| | | | |
|---|---|---|---|
| 3,498,290 | 3/1970 | Shaw et al. | 128/663 |
| 3,888,238 | 6/1975 | Meindl et al. | 128/663 |
| 3,948,248 | 4/1976 | Zuckerman et al. | 128/660 |
| 3,987,673 | 10/1976 | Hansen | 128/663 |
| 4,097,835 | 6/1978 | Green | 128/663 |

FOREIGN PATENT DOCUMENTS 1439592  6/1976  United Kingdom ................ 128/663

OTHER PUBLICATIONS

DeJong, D. A. et al., "A Directional Quantifying Doppler System for Measurement of Transport Velocity of Blood," Ultrasonics, vol. 13, #3, May 1975.
Olson, R. M. et al., "Human Carotid Artery Diameter and Flow by a Non-Invasive Technique," Med. Instrumentation, vol. 9, No. 2, Mar.-Apr. 1975.

Primary Examiner—Lee S. Cohen
Assistant Examiner—Francis J. Jaworski

[57] ABSTRACT

An ultrasonic wave probe comprises an ultrasonic wave transmitting vibrator and a pair of ultrasonic wave receiving vibrators in order to measure blood flow velocity. The receiving vibrators are adapted to receive reflected waves of an ultrasonic wave which is emitted from the transmitting vibrator and reflected from a measured point at different receiving angles and the difference between the receiving angles of the receiving vibrators is always kept to a given value. The ultrasonic wave probe further includes an ultrasonic wave transmitting and receiving vibrator for measuring blood vessel diameter deviation at the same time as the measurement of the blood flow velocity.

8 Claims, 5 Drawing Figures

ULTRASONIC WAVE PROBE

BACKGROUND OF THE INVENTION

1. Field of the Invention

This invention relates mainly to an ultrasonic wave probe for measuring blood flow velocity, and particularly to an ultrasonic wave probe which is suitable for use in an ultrasonic blood flow volume measuring device adapted to measure blood flow by means of an ultrasonic wave.

2. Description of the Prior Art

Prior to the description of the ultrasonic wave probe of this invention, the known blood flow volume measuring device by using an ultrasonic wave will first be mentioned.

Clear information on blood vessel mechanical properties of a carotid artery serves to reveal cerebral circulation characteristics (cerebral blood vessel characteristics) which effectively predict the cerebral blood vessel trouble such as cerebral arteriosclerosis. In other words, a mimic electric circuit model of the carotid artery system is arranged to have its input impedance characteristics approximate to the hydrodynamic input impedance characteristics obtained from the blood pressure and blood flow velocity of the carotid artery, and the cerebral circulation characteristics are measured using the parameters of the thus arranged electric circuit model.

The above electric circuit model is adapted to use the modified Windkessel type model. Therefore, a blood vessel diameter, carotid artery pulse wave, blood flow velocity (absolute flow velocity), etc. are first given to obtain a blood vessel resistance R, a blood vessel inertia L and a cerebral blood vessel capacitance C which are necessary for the modified Windkessel type model. Then, the input impedance characteristics of the blood vessel are obtained from the above constants with the result that the blood vessel mechanical properties can be made clear. Accordingly, in order to study the cerebral circulation characteristics, it is required to measure the blood pressure and blood flow amount of the carotid artery before revealing the aforesaid blood vessel diameter, carotid artery pulse wave and the like.

The blood pressure may be measured by a well-known strain gauge type blood-pressure measuring device. Meanwhile, the blood flow amount can be measured in a non-watching or non-invasive manner by using an ultrasonic wave. This device is referred to herein as an ultrasonic wave type blood flow amount measuring device.

As shown in FIG. 1, in this ultrasonic wave type blood flow amount measuring device, an ultrasonic wave from a probe (transducer) 3 is applied through the body surface to a carotid artery 1 and a reflected wave (a doppler signal) of an ultrasonic wave from the carotid artery 1, that is, from the blood flow in the blood vessel 1, is used to measure a blood flow velocity and blood flow amount or to display its waveform. In this case, however, measured values are greatly different as indicated by the following table according to an ultrasonic wave incident angle $\theta_T$ with respect to the carotid artery 1.

| Incident Angle $\theta_T(°)$ | Blood Flow Velocity (cm/sec) | Doppler Frequency (Hz) |
|---|---|---|
| 80 | 20.8 | 694 |
| 70 | 41.0 | 1368 |
| 60 | 60.0 | 2000 |
| 50 | 77.1 | 2571 |
| 40 | 91.9 | 3064 |

The above values are measured by using the blood of a human being having blood flow velocity of 60 cm/sec and by causing the ultrasonic wave probe 3 to touch the body surface where the blood flows through the blood vessel 1 in a direction of arrow a as shown in FIG. 1.

As seen from the above table, the blood flow velocity with the smallest error or no error is obtained when $\theta_T$ is 60°, but error is increased according as $\theta_T$ deviates from 60°. In this example, when the incident angle $\theta_T$ is deviated $\pm 10°$ from 60°, the measured values are changed about 25 to 30%. In other words, correct results cannot be obtained unless the ultrasonic wave incident angle $\theta_T$ is always held at 60°.

However, when handling the probe 3 in a practical case, a physician, for example, must manually hold the probe 3 to indirectly touch the surface adjacent the carotid artery 1 of a patient. Since manual manipulation is unsteady and easily variable under clinical conditions the incident angle $\theta_T$ becomes irregular case by case. For this reason, the blood flow velocity obtained by using the known probe 3 will be different at every measurement. As a result, the measurement accuracy is quite low.

Further, in the prior art, the ultrasonic wave probe for measuring the blood flow velocity and that for measuring the blood vessel diameter deviation are constructed separately from each other. Therefore, the diameter deviation and the blood flow velocity cannot be simultaneously measured at the same place of the blood vessel with the result that the measurement accuracy thereof is lowered.

SUMMARY OF THE INVENTION

Accordingly, it is an object of this invention to provide an ultrasonic wave probe by which a blood flow velocity can be correctly measured.

It is another object of this invention to provide an ultrasonic wave probe in which a blood vessel diameter deviation and a blood flow velocity can be simultaneously measured at the same place of the blood vessel thereby to improve the measurement accuracy.

According to a main feature of this invention, an ultrasonic wave probe is provided which comprises an ultrasonic wave transmitting vibrator and a pair of ultrasonic wave receiving vibrators in order to measure blood flow velocity. The receiving vibrators are supported by a supporting plate on a straight line together with the transmitting vibrator and adapted to receive reflected waves of an ultrasonic wave which is emitted from the transmitting vibrator and reflected from a measured point at different receiving angles, the difference between the receiving angles of the receiving vibrators being always kept to a given value.

According to another feature of this invention, the aforesaid ultrasonic wave probe includes an ultrasonic wave transmitting and receiving vibrator for measuring blood vessel diameter deviation, which is supported in the same direction as the ultrasonic wave transmitting vibrator and ultrasonic wave receiving vibrators are arranged and positioned outside one of the above receiving vibrators. The ultrasonic wave transmitting and receiving vibrator is arranged in such a manner that an ultrasonic wave emitted therefrom may meet the blood vessel to be measured at right angles and coincident with the point of the ultrasonic wave transmitting vibrator.

The other objects, features and advantages of the present invention will be apparent from the following description taken in conjunction with the accompanying drawings.

DESCRIPTION OF THE PREFERRED EMBODIMENT

A description will hereinafter be given on one example of an ultrasonic wave probe according to this invention with reference to FIG. 2 through FIG. 5.

As described above, the accuracy of the measurement of blood flow velocity can be improved if the measured values are kept constantly independent of the angles at which the ultrasonic wave probe touches the body surface. In order to eliminate error, the blood flow velocity may be measured by means of a pair of probes to make use of the reflected waves obtained from these probes. The reason why error can be eliminated by the above manner will be described later.

Figure 2:
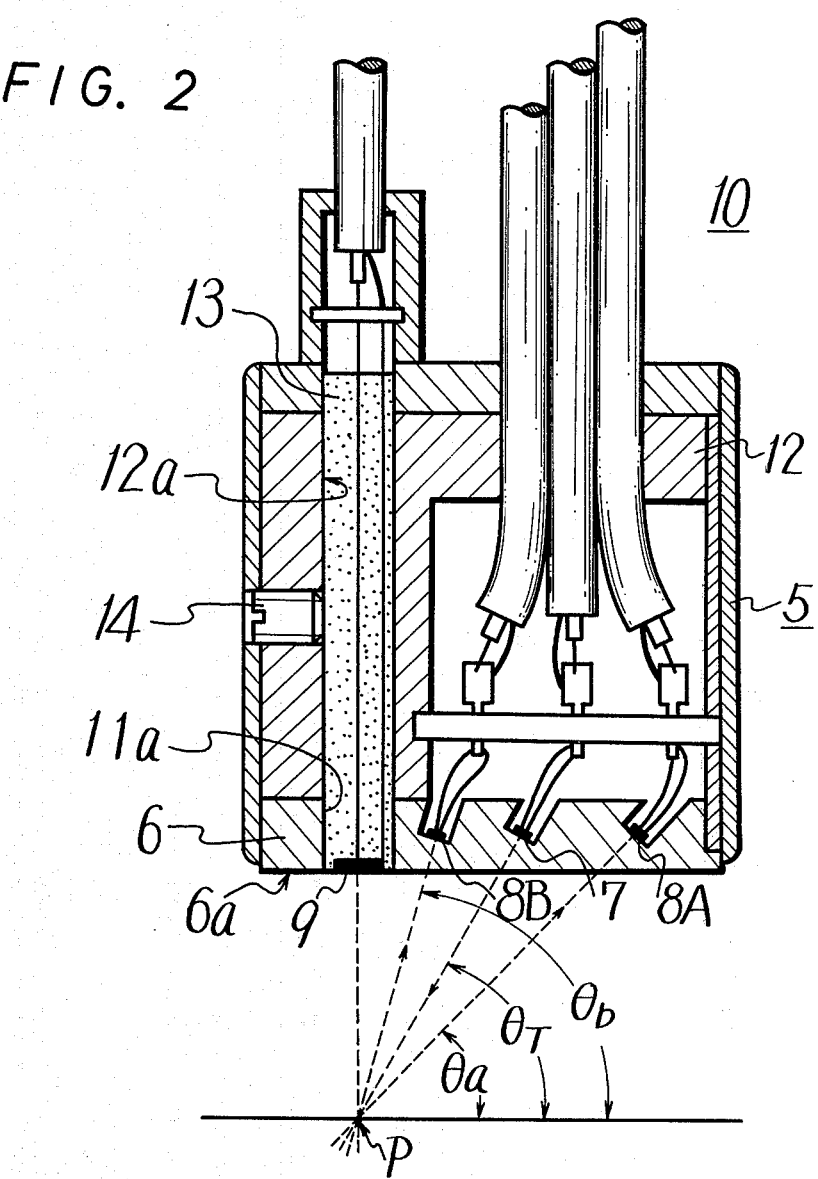
FIG. 2 is a longitudinal sectional view showing an ultrasonic wave probe according to this invention.
Figure 3:
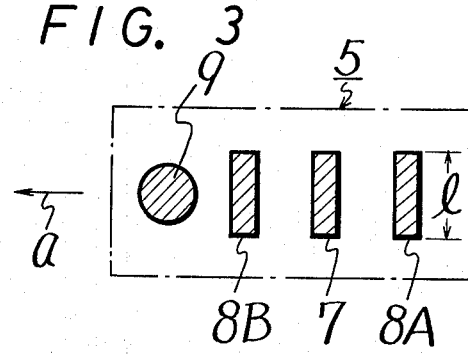
FIG. 3 is a bottom view of the ultrasonic wave probe shown in FIG. 2 showing a relationship among ultrasonic wave vibrators used therein.

In this invention, however, the ultrasonic wave probe uses at least three ultrasonic wave vibrators for the purpose of measuring the blood flow velocity. FIG. 2 shows one embodiment of this invention which makes use of three ultrasonic wave vibrators for measuring the blood flow velocity. Reference numeral 5 designates a metal case in the shape of a rectangular tube and 6 a vibrator supporting plate. The supporting plate 6 is provided at a given position with an ultrasonic wave transmitting vibrator 7. The vibrator 7 is located at a given angle with respect to a plane 6a so that the waves have a predetermined incident angle $\theta_T$ relative to the flow velocity. The supporting plate is also provided in front and rear of the ultrasonic wave transmitting vibrator 7 with a pair of ultrasonic wave receiving vibrators 8A, 8B which are mounted to the plate 6 so as to receive ultrasonic waves emitted by the ultrasonic wave transmitting vibrator 7 which are reflected from the measuring point P of the blood vessel at angles $\theta_a$, $\theta_b$ with respect to the blood vessel. Practical examples of the wave receiving angles $\theta_a$, $\theta_b$ will be described later. These vibrators 7, 8A, 8B are arranged on a straight line so as to be oriented along a blood flow direction a as shown in FIG. 3 when measuring the blood flow velocity.

Each of these vibrators 7, 8A, 8B has a size sufficient to measure the velocity of blood flowing through the whole section of the blood vessel 1. Therefore, these vibrators are each rectangular in section as shown in FIG. 3 and their length l in a direction normal to the direction a is determined on the basis of the blood vessel diameter $D_b$ to be measured. That is, since the vessel diameter $D_b$ is on the order of at most 7 to 10 mm, it is preferable to select the length l to the order of 10 mm for measuring the blood flow velocity throughout the whole section of the blood vessel. However, it is not necessary that the vibrators 7, 8A, 8B have the rectangular section as illustrated and may have any shape such as a circular one provided that the aforesaid object can be attained thereby. Each of the vibrators 7, 8A, 8B is composed of a ceramic vibrator having an inherent oscillating frequency of 5 MHz.

If the pair of ultrasonic wave receiving vibrators 8A, 8B are supported by the plate 6 in a manner as mentioned above with the ultrasonic wave transmitting vibrator 7 being interposed therebetween, it is not necessary to use an independent ultrasonic wave transmitting vibrator for each of the ultrasonic wave receiving vibrators 8A, 8B. In addition, the presence of only one ultrasonic wave transmitting vibrator 7 allows the ultrasonic wave receiving vibrators 8A, 8B to receive reflected waves from only the point P without being deviated therefrom.

Next, with the ultrasonic wave probe 10 constructed as described above, the blood flow velocity $V_b$ may be obtained in the following manner.

Figure 1:
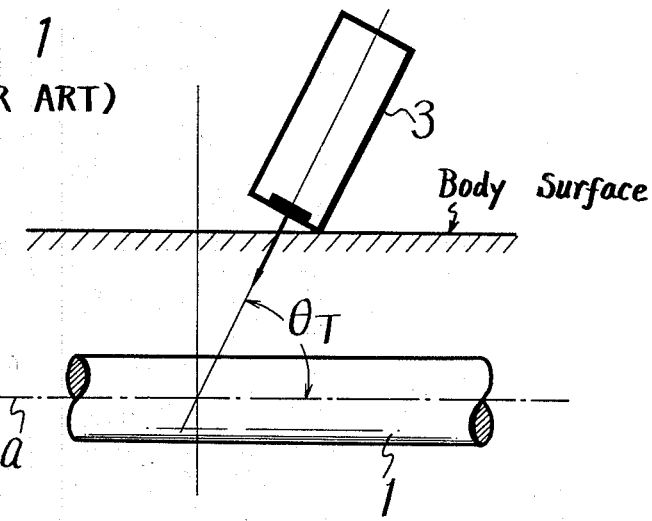
FIG. 1 is a diagrammatic view of an example of a prior art ultrasonic wave probe and its use.
Figure 4:
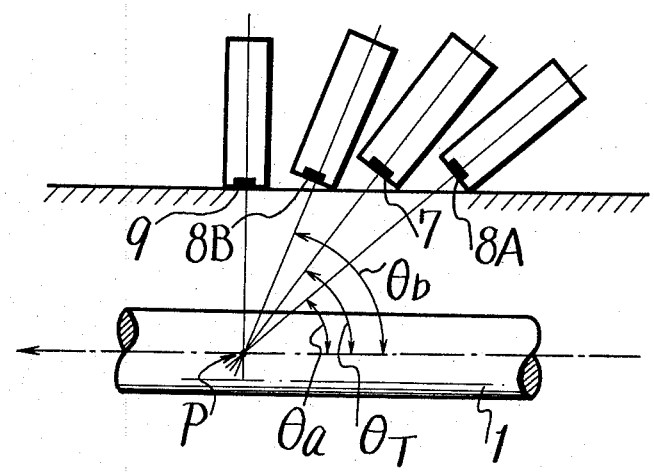
FIGS. 4 and 5 are diagrammatic views showing the operation of the ultrasonic wave probe, respectively.

Referring to FIG. 4, the incident angle of the vibrator 7 with respect to the blood vessel 1 is taken as $\theta_T$, and the wave receiving angles of the vibrators 8A, 8B as $\theta_a$ and $\theta_b$, respectively. If the blood flow is measured with $\theta_b - \theta_a = \theta$ being always kept at a given angle, a constant measured output can be obtained at all times irrespective of the touching angle of the ultrasonic wave probe 10 to the body surface.

It is known that the reflected wave of the ultrasonic wave emitted from the vibrator 7 at the measuring point P, or the doppler output, is proportional to flow velocity $V_b$ of the blood flowing through the carotid artery 1 and to the cosine of the ultrasonic wave receiving angle.

When the receiving vibrators 8A and 8B are located close to the transmitting vibrator 7, it is also known that the ultrasonic receiving angles and $\xi$ and $\eta$ of the vibrators 8A and 8B are respectively expressed as follows:

$$\xi = \frac{\theta_T + \theta_a}{2} \quad (4)$$

$$\eta = \frac{\theta_T + \theta_b}{2}$$

Thus, doppler outputs $S_a$, $S_b$ received by the vibrators 8A, 8B are given by the following formulas (1) and (2), respectively.

$$S_a = kV_b \cos\left(\frac{\theta_T + \theta_b}{2}\right) \quad (1)$$

$$S_b = kV_b \cos\left(\frac{\theta_T + \theta_a}{2}\right) \quad (2)$$

where $$k = 2f_s/C \quad (3)$$

$f_s$ is an inherent oscillating frequency of the vibrator 7, and

C is a transmission velocity of an ultrasonic wave in the blood.

Now, let it be assumed that $$\left.\begin{array}{l} \dfrac{\theta_T + \theta_b}{2} = \eta \\ \dfrac{\theta_T + \theta_a}{2} = \xi \end{array}\right\} \quad (4)$$

If it is assumed that the blood flow velocity $V_b$ is constant, the doppler outputs $S_a$ and $S_b$ depend on the receiving angles $\xi$ and $\eta$ respectively. Therefore, when the doppler outputs $S_a$ and $S_b$ are respectively rewritten to outputs $S_a$ and $S_b$ which respectively relate to the angles $\xi$ and $\eta$, the latter outputs are respectively expressed as follows:

$$S_a' = \dfrac{1}{k'} \cdot S_a \qquad (5)$$

$$S_b' = \dfrac{1}{k'} \cdot S_b$$

where $k' = k \cdot V_b$.

Figure 5:
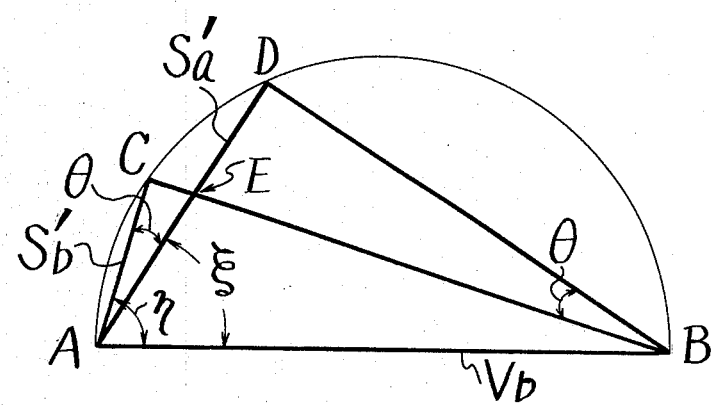

Therefore, the relation among the outputs $S_a'$, $S_b'$ and the angles $\xi$, $\eta$ can be explained by using the model shown in FIG. 5.

Then, a semi-circle with a diameter AB as shown in FIG. 5 is taken into consideration, and two points C and D are taken on the circumference of the semi-circle to satisfy the conditions $\angle CAB = \eta$ and $\angle DAB = \xi$. In this case, it is assumed that the blood flow velocity $V_b$ in the blood vessel 1 corresponds to the diameter AB, a doppler output $S_a'$ represented by a segment AD and a doppler output $S_b'$ presented by a segment AC are given by the following formulas in connection to the doppler outputs $S_a$ and $S_b$ represented by the formulas (1) and (2).

$$\left.\begin{array}{l} S_a' = \dfrac{S_a}{k} \\ S_b' = \dfrac{S_b}{k} \end{array}\right\} \quad (5)$$

That is, since the blood flow velocity $V_b$ is constant, if the velocity $V_b$ is taken on the diameter AB of the semi-circle of FIG. 5, the segment connecting the point A and a point on the semi-circle corresponds to each of the outputs $S_a'$ and $S_b'$. Accordingly, when the ultrasonic wave receiving angle is $\xi$ the segment AD (where $DAB = \xi$ and point D is on the semi-circle) corresponds to the output $S_a'$, and when the ultrasonic wave receiving angle is $\eta$, the segment AC (where $CAB = \eta$ and point C is on the semi-circle) corresponds to the output $S_b'$.

In FIG. 5, the blood flow velocity $V_b$ is given by $$\overline{V_b} = \sqrt{\overline{AD}^2 + \overline{DB}^2} \qquad (6)$$

If it is assumed that $\eta - \xi = \theta_b - \theta_a = \theta$, the segment DB is given by $$\overline{DB} = \dfrac{\overline{DE}}{\tan \theta} = \dfrac{S_a' - S_b'}{\cos \theta \cdot \tan \theta}$$

$$= S_a' \cot \theta - \dfrac{S_b'}{\sin \theta} \qquad (7)$$

As a result, the blood flow velocity $V_b$ defined by the formula (6) is given by $$\overline{V_b} = \sqrt{S_a'^2 + \left( S_a' \cot \theta - \dfrac{S_b'}{\sin \theta} \right)^2}$$

$$= \dfrac{S_a}{k} \sqrt{1 + \cot \theta - \dfrac{S_b}{S_a} \cdot \dfrac{1}{\sin \theta}} \qquad (8)$$

As seen from the formula (8), the blood flow velocity $V_b$ is a function of the mechanical angle $\theta$ defined by $\theta_a$ and $\theta_b$, but is not dependent on the touching angle of the probe 10 to the body surface. That is, the blood flow velocity $V_b$ is not dependent on any particular touching angle.

Accordingly, it is possible to measure the blood flow velocity irrespective of the change of the touching angle of the probe 10 at every measurement.

The angle $\theta$ is not limited to a specially defined value. In this embodiment, $\theta$ is selected at 20°. As described above, the measurement error becomes minimum when $\theta_T$ is 60° and hence the incident angle $\theta_T$ of the vibrator 7 is selected to about 60°. In this embodiment, the selection is made so that $\theta_T = 65°$, $\theta_a = 55°$ and $\theta_b = 75°$.

A description of a circuit arrangement for obtaining the blood flow velocity $V_b$ will be omitted because it has no direct relation with this invention.

Next, the blood vessel diameter deviation measuring device of this invention will be described again referring to FIGS. 2 and 3. A vibrator 9 for measuring the deviation of the blood vessel diameter is arranged at the outside of one of the ultrasonic wave receiving vibrators 8A, 8B, for example, 8B in this example, with respect to the ultrasonic wave transmitting vibrator 7. In practice, the vibrator 9 is aligned with the other vibrators 7, 8A, 8B and arranged in front of the vibrator 8B such that the ultrasonic wave emitted from the vibrator 9 may intersect the blood flow in the blood vessel 1 at right angles. In addition, the vibrator 9 is arranged such that the ultrasonic wave passing therethrough is radiated onto the same point P in the blood vessel 1 as the ultrasonic wave passing through the vibrator 7.

As shown in FIG. 2, the supporting plate 6 and its inner reinforcement member 12 are provided therethrough with bores 11a and 12a, which are filled with a packing material 13. The vibrator 9 is firmly secured to the front end of the packing material 13. Reference numeral 14 designates a screw for fixing the packing material 13 to the reinforcement member 12. The vibrator 9 is formed of barium titanate and functions to transmit and receive an ultrasonic wave. The vibrator 9 is intermittently excited by a pulse of 10 KHz and its inherent oscillating frequency is selected to be 6 MHz.

The vibrator 9 is utilized to provide a blood vessel diameter deviation output, or a deviation output conforming to a blood vessel pulsation. In this case, for example, a PLL circuit, though not shown, is used. That is, the reflected wave received by the vibrator 9 is supplied to a phase comparator of the PLL circuit together with an output of a delay oscillating circuit to carry out the phase comparison therebetween, and the thus phase-compared output is fed to the delay oscillating circuit to control its oscillation phase. With the above arrangement, it is possible to obtain an output having a pulse width conforming to the blood vessel pulsation, or the deviation output. Thus, the blood vessel diameter can be obtained from this deviation output. By the way, the amount of blood flow is a product of blood flow sectional area and blood flow velocity. A circuit arrangement for obtaining the blood flow amount will not be described because of the same reason as that for measuring the blood flow velocity.

According to this invention as described above, the pair of ultrasonic wave receiving vibrators 8A, 8B are arranged with the ultrasonic wave transmitting vibrator 7 being interposed therebetween and hence the ultrasonic wave transmitting vibrator 7 can be used in common with respect to the vibrators 8A, 8B. In addition, since only one vibrator 7 is used as the ultrasonic wave transmitting vibrator, the position of the incident point P becomes always constant and the blood flow velocity $V_b$ can be obtained on the basis of the reflected wave from the same point P. As a result, the measurement accuracy of the blood flow velocity $V_b$ is much improved.

Further, the ultrasonic wave vibrator 9 for measuring the blood vessel diameter deviation is arranged in the same case 5 as the other vibrators 7, 8A, 8B in such a manner that the ultrasonic wave emitted therefrom meets the blood vessel 1 at right angles. The vibrator 9 is also supported by the plate 6 so that its ultrasonic wave incident point in the blood vessel 1 may coincide with the ultrasonic wave incident point P of the vibrator 7. As a result, the blood flow velocity and the blood vessel deviation output can be obtained from the blood flowing condition at the same point in the blood vessel. This simultaneous measurement at the same place results in more accurate knowledge of blood flow amount than the prior art.

It will be apparent that many modifications and variations may be effected without departing from the scope of the novel concepts of this invention.

We claim as our invention:

1. An ultrasonic probe for determining characteristics of blood flow in a body vessel comprising a casing having one wall provided with a substantially planar exterior reference face adapted for contact with the body surface adjacent the vessel to be tested, an ultrasonic wave transmitting and a pair of ultrasonic wave receiving vibrators fixedly mounted in said one wall in linear alignment with said transmitting vibrator interposed between said pair of receiving vibrators, each of said vibrators being arranged at an angle to the plane of said exterior face so that their respective lines of wave action intersect at a point substantially at the center of blood flow in the vessel being tested, said transmitting receiver being set at an angle of about 60°–65° to the said substantially planar exterior reference face, and therefore to the approximate direction of blood flow and the angle between the respective lines of wave action of each of said receiving vibrators and the said substantially planar exterior reference face and therefore to the approximate direction of blood flow being both acute angles and said lines of action being angularly equi-distract from the line of action of said transmitting vibrator.

2. The probe according to claim 1 wherein the angle between the respective lines of action of said receiving vibrators is about 20°.

3. An ultrasonic wave probe as set forth in claim 1, wherein each of said vibrators is composed of a ceramic vibrator with an inherent oscillating frequency of 5 MHz, and wherein said ultrasonic wave transmitting vibrator is supported by said supporting means to have a pre-determined ultrasonic wave incident angle with respect to said substantially planar exterior reference face, and therefore to the approximate direction of blood flow within said blood vessel to be measured.

4. An ultrasonic wave probe as set forth in claim 1, wherein each of said vibrators has a rectangular section, the long sides of said rectangular section intersecting the line in which they are aligned at right angles.

5. An ultrasonic wave probe as set forth in claim 1 further including an ultrasonic wave transmitting and receiving vibrator for measuring blood vessel diameter deviation, and a second supporting means for supporting said last-mentioned vibrator, wherein said ultrasonic wave transmitting and receiving vibrator is arranged in the same alignment as said ultrasonic wave transmitting vibrator and ultrasonic wave receiving vibrators and positioned to the side of one of said receiving vibrators.

6. An ultrasonic wave probe as set forth in claim 5, wherein said ultrasonic wave transmitting and receiving vibrator is supported by said second supporting means so that an ultrasonic wave emitted from said transmitting and receiving vibrator is perpendicular to the reference face of said casing and is coincided to the line of action of transmitting and receiving vibrators.

7. An ultrasonic wave probe as set forth in claim 6, wherein said second supporting means is formed of a packing material filled into a bore provided at said first supporting means, and said ultrasonic wave transmitting and receiving vibrator is secured the end of said packing material adjacent the reference face.

8. An ultrasonic wave probe as set forth in claim 5, wherein said ultrasonic wave transmitting and receiving vibrator is composed of a barium titanate with an inherent oscillating frequency of 6 MHz.

* * * * *